US000001800H

United States Statutory Invention Registration [19]

[11] Reg. Number: H1,800

Salinas, III et al.

[45] Published: Aug. 3, 1999

[54] METHOD OF OXYCHLORINATION UTILIZING SPLIT FEEDS

[75] Inventors: Leopoldo Salinas, III; Thomas Earl Morris, both of Lake Jackson, Tex.

[73] Assignee: The Dow Chemical Company, Midland, Mich.

[21] Appl. No.: 08/893,320

[22] Filed: Jul. 16, 1997

Related U.S. Application Data

[63] Continuation-in-part of application No. 08/477,492, Jun. 7, 1995, abandoned.

[51] Int. Cl.[6] ..... C07C 17/15

[52] U.S. Cl. ..... 570/243

[58] Field of Search ..... 570/245

[56] References Cited

U.S. PATENT DOCUMENTS

| | | | |
|---|---|---|---|
| 3,190,931 | 6/1965 | Laine et al. | 260/659 |
| 3,992,463 | 11/1976 | Benaroya et al. | 260/659 |
| 4,123,467 | 10/1978 | Campbell et al. | 260/659 A |
| 4,206,180 | 6/1980 | Campbell et al. | 422/190 |
| 4,265,837 | 5/1981 | Legutke et al. | 570/243 |
| 4,329,527 | 5/1982 | Kuhn et al. | 570/245 |
| 4,740,644 | 4/1988 | Eichhorn et al. | 570/245 |
| 4,788,358 | 11/1988 | Riedl et al. | 570/241 |
| 4,849,562 | 7/1989 | Buhs et al. | 570/241 |
| 5,097,083 | 3/1992 | Stauffer | 570/241 |
| 5,099,085 | 3/1992 | Strasser et al. | 570/245 |
| 5,166,120 | 11/1992 | Deller et al. | 502/225 |
| 5,175,382 | 12/1992 | Hebgen et al. | 570/221 |
| 5,292,703 | 3/1994 | Young et al. | 502/303 |

FOREIGN PATENT DOCUMENTS

| | | | |
|---|---|---|---|
| 1 233 834 | 3/1988 | Canada | 260/660.3 |
| 1 468 465 | 11/1968 | Germany . | |
| 3346464 | 6/1985 | Germany | 570/245 |
| WO 96/26171 | 8/1996 | WIPO | 17/156 |

*Primary Examiner*—Charles T. Jordan
*Assistant Examiner*—Meena Chelliah
*Attorney, Agent, or Firm*—Dale H. Schultz; William B. Miller; Stephen S. Grace

[57] ABSTRACT

A method for oxychlorinating ethylene to ethylene dichloride utilizing a two reactor oxychlorination system in which the oxygen and hydrogen chloride feeds are split between the reactors such that the volume ratio of HCl fed to the first reactor to the HCl fed to the second reactor, and the volume ratio of $O_2$ fed to the first reactor to the $O_2$ fed to the second reactor are both in the range of about 50:50 to about 99:1.

15 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

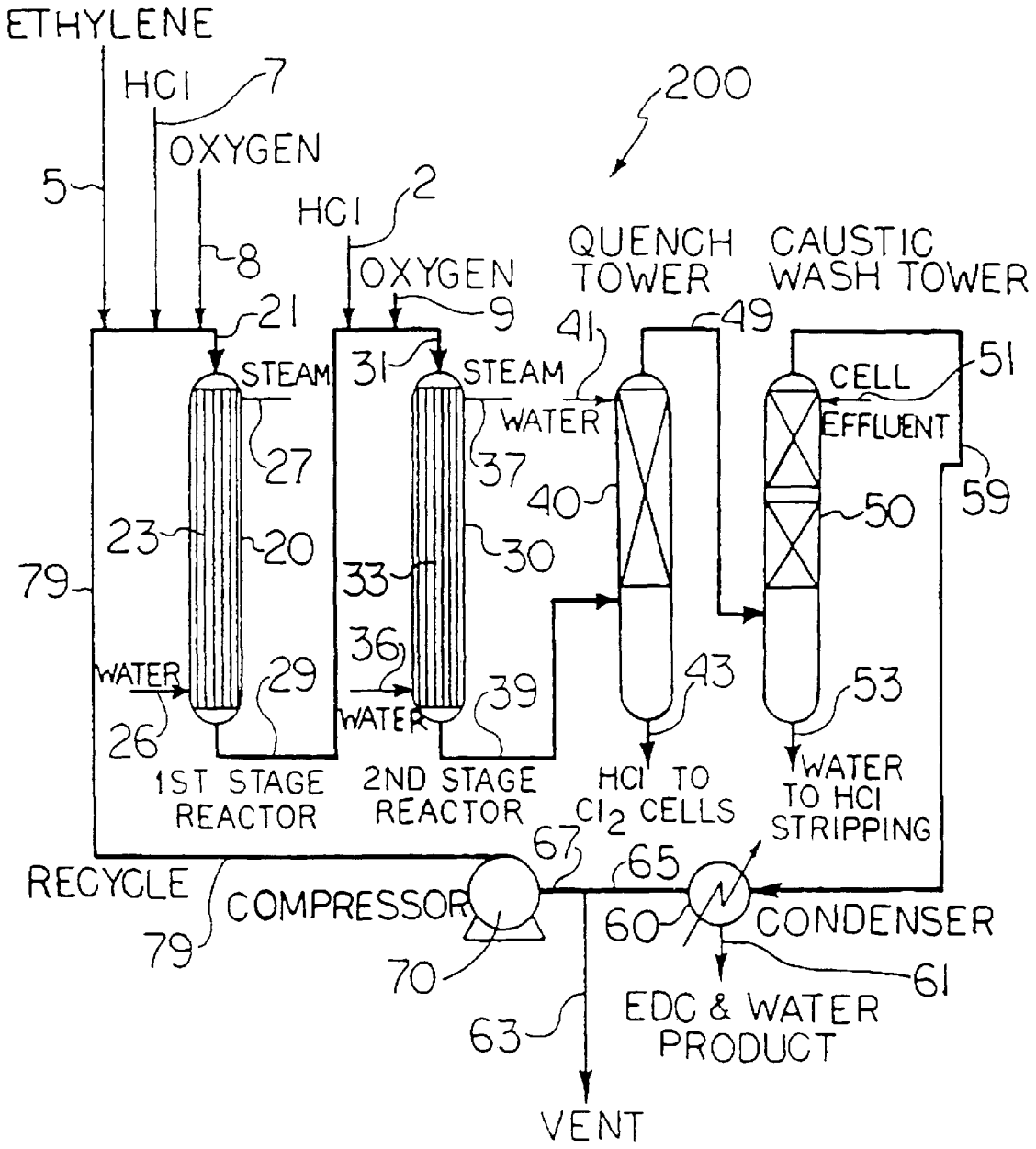
ETHYLENE
HCl
7
OXYGEN
5
8
HCl
2
OXYGEN
9
200
QUENCH TOWER
CAUSTIC WASH TOWER
21
STEAM
31
STEAM
41
49
CELL
51
WATER
EFFLUENT
27
37
40
50
59
23
20
30
79
33
36
WATER
29
39
43
53
26
WATER
1ST STAGE REACTOR
2ND STAGE REACTOR
HCl TO $Cl_2$ CELLS
WATER TO HCl STRIPPING
67
65
RECYCLE
COMPRESSOR
CONDENSER
79
60
70
61
EDC & WATER PRODUCT
63
VENT

METHOD OF OXYCHLORINATION UTILIZING SPLIT FEEDS

This application is a continuation-in-part of U.S. application Ser. No.08/477,492 filed Jun. 7, 1995, now abandoned, from which priority is claimed.

FIELD OF THE INVENTION

The present invention relates to a method of oxychlorination. Specifically, the present invention relates to a method of ethylene oxychlorination utilizing a split feed of oxygen and hydrochloric acid to a two reactor system.

BACKGROUND OF THE INVENTION 1,2-dichloroethane, commonly known as ethylene dichloride ("EDC") is a compound manufactured industrially on a scale of several million tons per year, which, on pyrolysis is converted into vinyl chloride monomer and hydrochloric acid. Vinyl chloride monomer is polymerized into poly (vinyl) chloride ("PVC"), a widely used polymer.

Catalysts and processes for the production of chlorinated hydrocarbons by oxychlorination have been well established for a number of years. Specifically, oxychlorination of ethylene with oxygen and hydrochloric acid in the presence of a catalyst to produce 1,2-dichloroethane is widely practiced in commercial installations throughout the world.

The catalyst composition, that is, the catalyst itself and its support material, can be in the form of a fluidized bed of particles which are fluidized during the reaction, or in the form of a fixed bed of particles. In the oxychlorination of ethylene with such a catalytic fixed bed, the catalysts advantageously contain copper II chloride on a carrier in combination with promoters, such as potassium chloride.

In oxychlorination processes, major concerns include productivity, efficient catalyst utilization, HCl conversion, and capital costs.

EP 0146925 filed Dec. 19, 1984 discloses a method for the oxychlorination of ethylene utilizing oxygen-enriched air. In two-reactor installations, the total quantity of ethylene and hydrogen chloride is fed to the first reactor while the oxygen is divided between the two reactors. This reference teaches utilization of three or more reactors when dividing both hydrogen chloride and oxygen between the first two serially connected reactors.

There is a need in the art for an improved method of oxychlorinating ethylene.

SUMMARY OF THE INVENTION

It is an object of the present invention to provide for an improved method of oxychlorinating ethylene.

It has been discovered that two reactors, rather than three or more reactors, may be effectively utilized when splitting both HCl and $O_2$ between reactors, thereby decreasing complexity in reactor control and saving capital in reactor equipment costs plus savings in feed piping, instrumentation, exchangers and other associated equipment, while surprisingly maintaining high HCl conversions. This and other objects of the present invention will become apparent to those of skill in the art upon review of this patent specification, including its drawing and claims.

The present invention is a method of oxychlorinating ethylene to ethylene dichloride utilizing no more than two oxychlorination reactors and splitting the oxygen and hydrogen chloride feeds between the two reactors. Specifically, the method includes feeding ethylene, hydrogen chloride and oxygen to the first reactor where the ethylene, hydrogen chloride and oxygen are contacted together, preferably in the presence of a copper containing catalyst, to produce a first reactor product stream. The method further includes feeding hydrogen chloride, oxygen, and the first reactor product stream to the second reactor where the ethylene, hydrogen chloride, oxygen and first reactor stream are contacted together, preferably in the presence of a copper containing catalyst, to produce a second reactor product stream. Optionally, ethylene feed may also be split between the reactors. Additionally, recycle streams may be utilized and split between the reactors.

The volume ratio of the hydrogen chloride fed to the first reactor to the hydrogen chloride fed to the second reactor is in the range of about 50:50 to 99:1, and the volume ratio of the oxygen fed to the first reactor to the oxygen fed to the second reactor is in the range of about 50:50 to 99:1. The second reactor product stream may then be subjected to further processing to recover the ethylene dichloride product as is well known in the oxychlorination art, including water quenching and caustic washing.

BRIEF DESCRIPTION OF THE DRAWING

The FIGURE is a schematic representation of one embodiment of the oxychlorination process of the present invention, showing first reactor 20, second reactor 30, quench tower 40, caustic wash tower 50, condenser 60 and recycle pump 70.

DETAILED DESCRIPTION OF THE INVENTION

The method of the present invention is better understood by reference to the FIGURE.

Tube type reactors, with catalyst in the tubes and a cooling medium provided to the outside of the tubes are well known as being suitable for oxychlorination. While first reactor 20 and second reactor 30 may be any suitable types of reactors, they are preferably tube reactors having catalyst within a multiplicity of tubes 23 and 33, respectively. Advantageously, tubes 23 and 33 have diameters in the range of about 0.5 inch to about 3 inches (13 to 80 millimeters), with diameters in the range of about 1.0 to 2.0 inches (25 to 50 millimeters) not uncommon. Preferably, the diameters will be in the range of 1.5 inches to 2.0 inches (38 to 50 millimeters). Tube lengths effectively range from 10 to 60 feet (3 to 18 meters), preferably from 20 to 40 feet (6 to 12 meters), and are most preferably 30 feet (9 meters).

The exothermic heat of reaction is removed utilizing a heat transfer media applied to the shell side of first reactor 20 and second reactor 30. As the type of heat transfer media is not critical, any suitable media known to those of skill in the art may be utilized. Examples of suitable heat transfer media are high boiling mineral oils, silicon oils, and water. Water, which is converted into medium-pressure steam by adsorption of heat, is preferred. As shown in the FIGURE, water streams 26 and 36 are provided to reactors 20 and 30, respectively, and exit reactors 20 and 30 as steam streams 27 and 37, respectively.

In the practice of the method of the present invention, the hydrogen chloride and oxygen feeds are split between first reactor 20 and second reactor 30.

As shown in the FIGURE, feed streams of ethylene 5, HCl 7 and oxygen 8, as well as recycle stream 79 are fed to first reactor 20 as feed stream 21. The resultant product stream 29 of first reactor 20 is combined with hydrogen chloride stream 2 and oxygen stream 9 and fed to second reactor 30 as feed stream 31. The molecular oxygen introduced into the reactors 20 and 30 may be introduced as such or in the form of an oxygen-containing gas mixture such as air.

The total amounts of ethylene, hydrogen chloride, and oxygen provided to both reactors, will advantageously be such that, based on the amount of hydrogen chloride, a slight stoichiometric excess of ethylene and oxygen are provided. Such excess is conveniently in the range of about 1 to 5 mole %, preferably about 2 to 4 mole %.

The hydrogen chloride utilized is split between feed stream 7 to first reactor 20 and feed stream 2 to the second reactor 30. In the practice of the present invention, the total hydrogen chloride provided is split between the first reactor 20 and the second reactor 30 in a volume ratio in the range of 50:50 to 99:1. Preferably, the total hydrogen chloride provided is split between the first reactor 20 and the second reactor 30 in a volume ratio in the range of 50:50 to 80:20, and most preferably in the range of 50:50 to 75:25. Volume ratio means percent of total volume fed to the first reactor: percent of total volume fed to second reactor.

The oxygen utilized is split between feed stream 8 to first reactor 20 and feed stream 9 to the second reactor 30. In the practice of the present invention, the total oxygen provided is split between the first reactor 20 and the second reactor 30 in a volume ratio in the range of 50:50 to 99:1. Preferably, the total oxygen provided is split between the first reactor 20 and the second reactor 30 in a volume ratio in the range of 50:50 to 80:20, and most preferably in the range of 50:50 to 75:25. In addition, the percent of total HCl fed to the first reactor is preferably about the same as the percent of total O2 fed to the first reactor. In other words, the percent of total HCl fed to the first reactor divided by the percent of total O2 fed to the first reactor is preferably from about 0.95 to about 1.5; more preferably about 1.

Contacting times within the reactors 20 and 30 will be any suitable to provide the desired oxychlorination. "Contacting time" is defined as the ratio of the free or usable volume of the reactor to the volumetric flow rate of the feed gases at the operating conditions. Contacting times are generally dictated by economics and the desired conversion, but are conveniently no more than a few seconds. Contacting times will preferably range from 2 to 6 seconds, and are more preferably in the range of 3 to 5 seconds.

The operating temperatures within first and second reactors 20 and 30 will advantageously range from 180° C. to 350° C., preferably in the range of 200° C. to 270° C.

Once the reactants proceed through first reactor 20 and second rector 30, the resultant product stream 39 may be processed in any suitable manner as is known in the art for recovery of the ethylene dichloride. Such known processing advantageously includes water quenching and caustic washing.

Referring again to the FIGURE, product stream 39 from second reactor 30 is fed to quench tower 40, wherein product stream 39 is cooled by contact with water stream 41. Unconsumed hydrogen chloride and the bulk of the reaction water are condensed and exit though the bottom of quench tower 40 as bottoms stream 43. Uncondensed gases exit quench tower 40 through stream 49 to be contacted with caustic stream 51 in caustic wash tower 50. The water stream 53 is further processed by RCl stripping to remove chlorinated organics.

Uncondensed gas stream 59 is condensed at condenser 60 to remove a water and ethylene dichloride product stream 61. Uncondensed stream 65, containing ethylene, carbon monoxide and dioxide, and small amounts of ethylene dichloride as well as other contaminants, is first vented to remove gases as vent stream 63, and then stream 67 is recycled back to first reactor 20 as recycle stream 79 using compressor 70.

The composition and shape of the oxychlorination catalyst is not critical, and any suitable catalyst, having a range of catalytic compositions, and having a range of effective shapes may be utilized. Accordingly, in the practice of the present invention, any oxychlorination catalyst composition may be utilized, preferably, an alumina support impregnated with a copper catalyst. Such catalysts are well know to those of skill in the art.

The oxychlorination catalyst will generally comprise sufficient copper to provide the desired catalytic effect. The copper is typically burdened as cupric chloride. Copper will commonly comprise in the range of 1 weight percent to 12 weight percent of the dry weight of the catalyst, preferably in the range of 1 weight percent to 8 weight percent of the dry weight of the catalyst. When utilized, an alkali metal, preferably potassium, will commonly comprise in the range of 0.2 weight percent to 5 weight percent of the dry weight of the catalyst, preferably in the range of 0.8 weight percent to 3 weight percent of the dry weight of the catalyst and is typically potassium chloride.

The catalyst in reaction tubes 23 and 33, have in the direction of flow, gradually rising copper concentration within sections of the tubes, thus ensuring better distribution of heat over the whole catalyst and better dissipation of reaction heat as a consequence.

For example when using copper and potassium as the catalysts in reactors 20 and 30, the ratio of potassium to copper in the first third of the reactor is advantageously in the range of 1.2 to 0.8, in the second third in the range of 0.3 to 0.8, and in the last third in the range of 0.05 to 0.3.

Additionally, a variety of advantageous catalyst shapes may be utilized, including as nonlimiting examples, spheres, columns, rings, annular columns, and annular columns with internal supports. Preferable geometric shapes suitable for use in the method of the present invention include spheres, rings and annular columns having a height and diameter in the range of about 6.5 to 10 millimeters.

EXAMPLE

An example of the process operating with a 7 millimeter diameter spherical catalyst is given as an illustration. For the catalysts referred to in this example as catalysts A, B, and C, the weight percents of copper chloride and potassium chloride are 3.6/1.8%, 3.6/0.7%, and 6.0/0.2%, respectively.

The two reactors each consisted of tubes 1.5 inches (38 millimeters) in outside diameter. The reactor tubes utilized in collecting data sets I and II had an inner diameter of 1.4 inches (35 mm) and 1.3 inches (33 mm) respectively. Heat generated in the reaction was removed through the generation of steam in a shell that encased the tubes. The reactors are each divided into 3 sections of 10 feet (3 meters) in length. Catalyst A was used in the first two sections of the first reactor in volumetric concentrations of 55 and 75% respectively. A mixture of Catalyst A and B in the volumetric ratio of 1.271/1 was used in the bottom section of the first reactor. This first section of the second reactor utilized Catalyst A and B as well, this time in a ratio of 0.55/1. The second section of the second reactor utilized Catalysts B and C in the ratio of 0.67/1 and Catalyst C was used in the last section of the second reactor.

Feeds of ethylene, oxygen and HCl were initiated to the reactor system and the system was allowed to stabilize before data was collected. The HCl Flow was 450 pounds/day/tube and system pressure was 50 psig. For comparison, stoichiometric ratios of O2/HCl and C2H4/HCl are 0.25 and 0.5, respectively. Other operating data and results are listed below:

| Total mole O2/HCl | C2H4/HCl (mol/mol) | % HCl fed to R1 | % O2 fed to R1 | Shell Temp. R1 | Shell Temp. R2 | HCl Conversion | Productivit lb. EDC/lb. catalyst |
|---|---|---|---|---|---|---|---|
| | | | DATA SET I | | | | |
| .28 | .47 | 100 | 100 | 207.5 | 203.2 | 97.33 | 36.0 |
| .25 | .49 | 75 | 76 | 199.4 | 203.8 | 99.50 | 56.7 |
| .28 | .52 | 75 | 76 | 206.5 | 206.2 | 99.38 | 60.0 |
| .28 | .49 | 60 | 62 | 207.0 | 206.6 | 99.17 | 57.8 |
| .26 | .49 | 60 | 57 | 207.8 | 208.4 | 98.80 | 75.2 |
| .25 | .47 | 60 | 61 | 206.7 | 208.8 | 99.39 | 70.4 |
| .27 | .50 | 50 | 51 | 205.9 | 208.1 | 99.60 | 74.7 |
| .26 | .47 | 50 | 51 | 207.8 | 208.5 | 99.53 | 70.1 |
| | | | DATA SET II | | | | |
| .27 | .50 | 55 | 55 | 214.1 | 213.4 | 96.81 | 93.4 |
| .27 | .51 | 75 | 53 | 214.3 | 213.4 | 99.12 | 110.5 |
| .27 | .50 | 73 | 57 | 214.5 | 213.3 | 99.71 | 108.2 |
| .27 | .50 | 72 | 58 | 215.4 | 212.2 | 98.85 | 64.7 |
| .27 | .50 | 72 | 57 | 215.4 | 213.8 | 99.64 | 65.8 |
| .26 | .49 | 58 | 51 | 211.6 | 214.2 | 99.84 | 111.5 |
| .26 | .48 | 55 | 50 | 213.7 | 214.3 | 99.20 | 103.3 |
| .25 | .48 | 55 | 50 | 214.9 | 214.3 | 98.75 | 105.1 |
| .26 | .49 | 54 | 54 | 209.8 | 209.8 | 98.52 | 86.1 |
| .27 | .49 | 54 | 54 | 209.6 | 211.1 | 97.45 | 85.0 |

The first row of data in the table showing 100% HCl and 100% O2 fed to first reactor (R1) is for comparison with the split flow method of the present invention.

The data show a trend of improved HCl conversion and improved productivity (pounds EDC/pound catalyst) when utilizing the split HCl and O2 feed method of the invention over feeding all reactants to the first reactor. In three reactor split flow systems like EP 0146925, the third reactor is typically to achieve additional conversion. Therefore, one of ordinary skill in the art would expect the HCl conversion to decrease significantly if the third reactor were removed. Surprisingly, high HCl conversion is maintained without the added capital costs associated with a third reactor. The method of the invention also permits greater flexibility in catalyst choice.

Low process temperatures were maintained and excellent reactor performance was achieved.

We claim:

1. A method of oxychlorination comprising:

providing an oxychlorination reactor system having a first reactor in fluid communication with a second reactor, said reactor system for converting ethylene, hydrogen chloride, and oxygen into a ethylene dichloride product stream from said second reactor;

feeding a quantity of hydrogen chloride to said reactor system;

feeding ethylene to said reactor system in less than 5% stoichiometric excess to said quantity of hydrogen chloride;

feeding a quantity of oxygen to said reactor system in stoichiometric excess to said quantity of hydrogen chloride;

reacting ethylene, hydrogen chloride and oxygen in said first reactor by contacting ethylene, hydrogen chloride, and oxygen together in the presence of an oxychlorination catalyst to produce a first reactor product stream containing ethylene;

reacting hydrogen chloride, oxygen and the first reactor product stream in said second reactor by contacting said first reactor product stream, hydrogen chloride and oxygen together in the presence of an oxychlorination catalyst to produce said ethylene dichloride product stream; and recycling ethylene from said ethylene dichloride product stream to provide recycled ethylene to said first reactor;

wherein the ratio of the hydrogen chloride fed to the first reactor to the hydrogen chloride fed to the second reactor is in the range of about 50:50 to about 99:1, and wherein the ratio of the oxygen fed to the first reactor to the oxygen fed to the second reactor is in the range of about 50:50 to about 99:1.

2. The method of claim 1 wherein the ethylene, hydrogen chloride and oxygen are contacted together in the presence of a copper containing catalyst.

3. The method of claim 1 wherein the volume ratio of the hydrogen chloride fed to the first reactor to the hydrogen chloride fed to the second reactor is in the range of 50:50 to 80:20, and wherein the volume ratio of the oxygen fed to the first reactor to the oxygen fed to the second reactor is in the range of 50:50 to 80:20.

4. The method of claim 1 wherein the volume ratio of the hydrogen chloride fed to the first reactor to the hydrogen chloride fed to the second reactor is in the range of 50:50 to 75:25, and wherein the volume ratio of the oxygen fed to the first reactor to the oxygen fed to the second reactor is in the range of 50:50 to 75:25.

5. The method of claim 1 wherein the operating temperatures within the first reactor and the second reactor are in the range of from 180° C. to 350° C.

6. The method of claim 1 wherein the percent of total HCl fed to the first reactor is about the same as the percent of total O2 fed to the first reactor.

7. The method of claim 1 wherein the percent of total hydrogen chloride fed to the first reactor divided by the percent of total oxygen fed to the first reactor is from about 0.95 to about 1.5.

8. The method of claim 3 wherein the percent of total hydrogen chloride fed to the first reactor divided by the percent of total oxygen fed to the first reactor is from about 0.95 to about 1.5.

9. The method of claim 1 further comprising:

(c) contacting the second reactor product stream with water to form a quenched product stream.

10. The method of claim 9 further comprising:

(d) contacting the quenched product stream with a caustic to form a washed stream.

11. The method of claim 10 further comprising:

(e) condensing the washed stream to form an ethylene dichloride product stream and a recycle gas stream.

12. The method of claim 11 further comprising:

(f) recycling the recycle gas stream to the first reactor.

13. The method of any one of claims 1 to 12 further including the step of recycling ethylene from said ethylene dichloride product stream to provide recycled ethylene to said second reactor wherein said recycled ethylene is split between said first reactor and said second reactor.

14. The method of any one of claims 1 to 12 wherein the step of feeding ethylene to said reactor system in less than 5% stoichiometric excess to said quantity of hydrogen chloride feeds said ethylene to said first reactor and said second reactor in split fashion.

15. The method of any one of claim 14 further including the step of recycling ethylene from said ethylene dichloride product stream to provide recycled ethylene to said second reactor wherein said recycled ethylene is split between said first reactor and said second reactor.

* * * * *